United States Patent [19]

Figgie, III et al.

[11] Patent Number: 4,892,549
[45] Date of Patent: Jan. 9, 1990

[54] DUAL-RADIUS ACETABULAR CUP COMPONENT

[75] Inventors: Harry E. Figgie, III, Pepper Pike, Ohio; Alfred J. Zarnowski, North Plainfield; Matthew V. Lyons, Hoboken, both of N.J.

[73] Assignee: Osteonics Corp., Allendale, N.J.

[21] Appl. No.: 304,752

[22] Filed: Jan. 31, 1989

[51] Int. Cl.$^4$ ............................................. A61F 2/34
[52] U.S. Cl. ...................................................... 623/22
[58] Field of Search ..................... 623/16, 18, 20, 22, 623/23

[56] References Cited

U.S. PATENT DOCUMENTS

| | | | |
|---|---|---|---|
| 3,891,997 | 7/1975 | Herbert | 623/22 |
| 4,437,193 | 3/1984 | Olt | 623/22 |
| 4,704,127 | 11/1987 | Averill et al. | 623/22 |
| 4,795,469 | 1/1989 | Oh | 623/22 |
| 4,795,470 | 1/1989 | Goymann et al. | 623/22 |

FOREIGN PATENT DOCUMENTS 1527498 10/1978 United Kingdom ................ 623/22

Primary Examiner—Richard J. Apley
Assistant Examiner—David J. Isabella
Attorney, Agent, or Firm—Samuelson & Jacob

[57] ABSTRACT

An acetabular cup has a shell component with an outer surface including a first spherical surface portion and a second spherical surface portion, and an acetabulum is prepared with an inner surface having a spherical configuration complementary to the second spherical surface portion of the shell component, the radius of the first spherical surface portion being slightly greater than the radius of the second spherical surface portion such that upon nesting of the second spherical surface portion of the shell component in contiguous relationship with the inner surface of the acetabulum, the first spherical surface portion engages the inner surface of the acetabulum in an interference fit to secure the shell component within the prepared acetabulum.

14 Claims, 2 Drawing Sheets

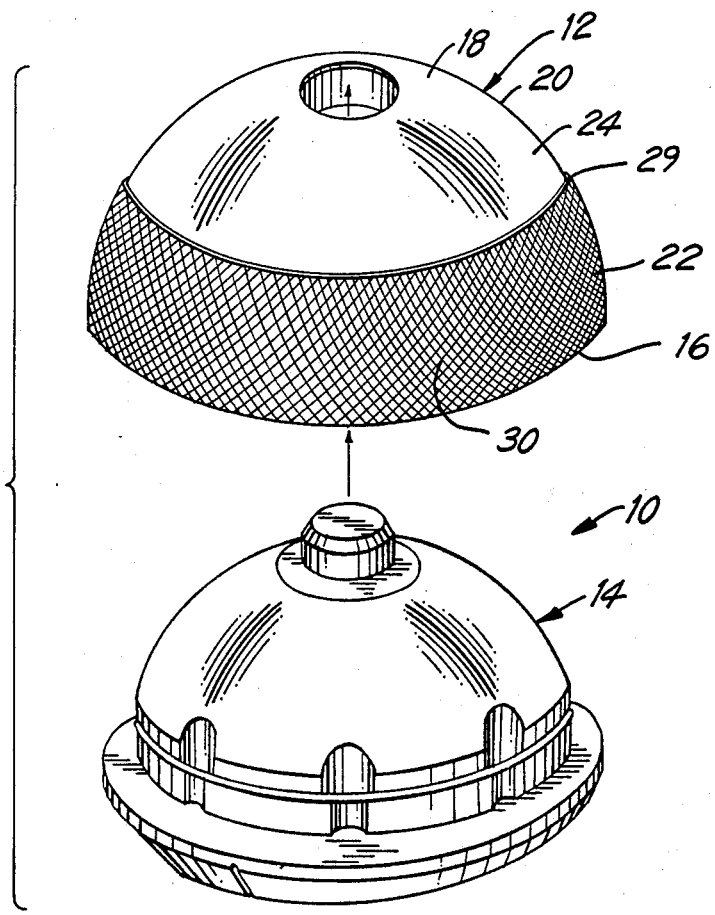
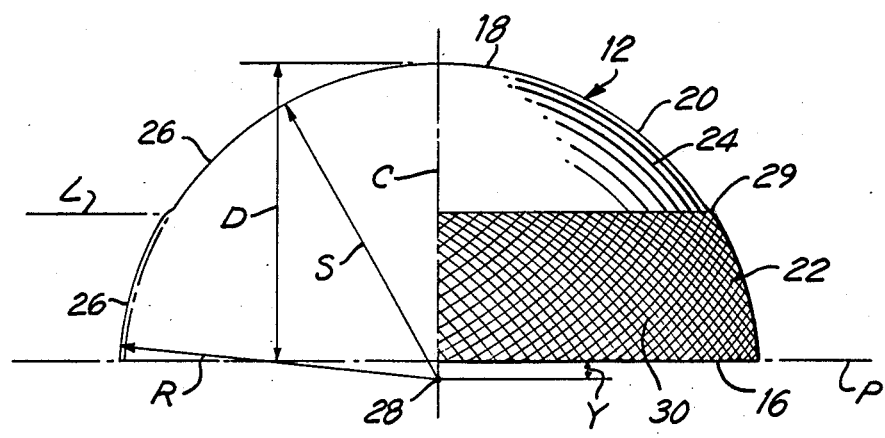

DUAL-RADIUS ACETABULAR CUP COMPONENT

The present invention relates generally to prosthetic implant devices and pertains, more specifically, to an acetabular cup component to be implanted within the acetabulum.

Acetabular cups routinely are employed to replace the socket provided by the natural acetabulum in the implant of hip joint prostheses. The securement of the acetabular cup within the bone of the hip joint has been accomplished through the use of cement. The shortcomings of the various available cements are well-documented and it would be advantageous to have available a construction enabling an acetabular cup to be implanted and fixed within the acetabulum without the use of cement.

One such construction is disclosed in U.S. Pat. No. 4,704,127, wherein there is illustrated an acetabular cup having a dual-geometry outer surface configuration, including a generally frusto-conical surface portion and a generally spherical surface portion. The method of implanting the acetabular cup requires a two-step preparation of the acetabulum to provide both a spherical surface portion and a frusto-conical surface portion along the acetabulum for the reception of the corresponding surface portions of the acetabular cup component. Further, once the acetabulum is prepared to receive the acetabular cup component, the angular orientation of the central axis of the cup is fixed; that is, the accuracy of the angular orientation of the central axis of the implanted acetabular cup component is determined by the accuracy of the orientation of the instruments employed in the preparation of the acetabulum. Thus, it becomes important that the surgeon exercise extreme care to assure proper orientation of the cutting instruments during preparation of the acetabulum.

The present invention provides an acetabular cup component with an outer surface configuration which enables implant and securement without the use of cement or another adhesive, and does so with increased efficacy over commonly available spherical acetabular cup components, while requiring a reduced number of steps in the implant procedure and rendering the angular orientation of the surgical cutting instruments less critical than in the aforesaid dual-geometry acetabular cup component. Accordingly, the present invention accomplishes several objects and advantages, some of which may be summarized as follows: provides an acetabular cup component capable of being implanted and secured in place without the use of cement or another adhesive, utilizing a simplified implant method; provides an acetabular cup component capable of being implanted and secured in place with an interference fit; enables simplification of the preparation of the acetabulum with less invasion of the bone of the acetabulum; reduces the criticality of the angular orientation of the cutting instruments employed to prepare the acetabulum for implant, while still realizing the advantages of an interference fit between the acetabular cup component and the acetabulum; enables a quicker preparation of the acetabulum without sacrificing efficacy; places the interference fit at a preferred location within the bone available in the acetabulum while attaining congruity between the acetabular cup component and the prepared acetabulum essentially along the entire prepared acetabular surface, thus achieving appropriate bone apposition for proper implant affixation; enables a cup configuration of simplified design and construction for ease of manufacture with precision and reliability; enables a rugged construction in an acetabular cup component for reliable service over a long service life.

The above objects and advantages, as well as further objects and advantages, are attained by the present invention which may be described briefly as a shell component for use in an acetabular cup assembly of a prosthetic joint, the shell component being capable of implant into an acetabulum and securement therein by an interference fit, the shell component comprising: a lower rim; an apical region spaced upwardly in an axial direction a given distance from the lower rim; and an outer surface having a first generally spherical surface portion extending upwardly from the lower rim to an intermediate location spaced approximately one-half the distance between the lower rim and the apical region, and a second generally spherical surface portion extending upwardly from the intermediate location to the apical region, the first generally spherical surface portion having a radius slightly greater than the radius of the second generally spherical surface portion.

The invention will be understood more fully, while still further objects and advantages will become apparent, in the following detailed description of a preferred embodiment of the invention illustrated in the accompanying drawing, in which:

FIG. 1 is an exploded perspective view of an acetabular cup assembly including a shell component constructed in accordance with the present invention;

FIG. 2 is an enlarged, partially diagrammatic, elevational view of the shell component;

Figure 3:
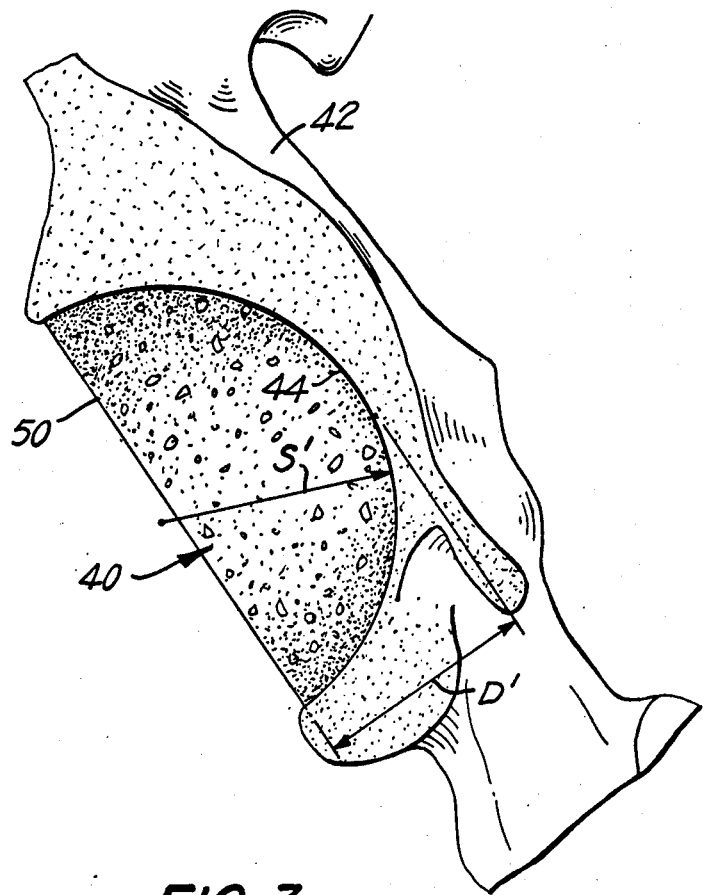
FIG. 3 is an illustration of a portion of a hip bone showing the preparation of the acetabulum for reception of the shell component.

Referring now to the drawing, and especially FIG. 1 thereof, an acetabular cup assembly 10 is shown having a shell component 12 constructed in accordance with the invention, and a bearing component in the form of bearing insert 14. Initially, the shell component 12 will be implanted and secured within the acetabulum, as will be explained below, and the bearing insert 14 will be assembled with the shell component 12, interoperatively, in the manner described in U.S. Pat. No. 4,695,282.

As best seen in FIG. 2, as well as in FIG. 1, shell component 12 includes a lower rim 16 and an apical region 18 spaced upwardly in an axial direction a given distance D from the lower rim 16. The outer surface 20 of the shell component 12 includes a first or lower generally spherical surface portion 22 and a domed, second or upper generally spherical surface portion 24 which, together, establish a unique dual-radius surface contour 26 along the outer surface 20 of the cup component 12.

The lower spherical surface portion 22 extends upwardly along an essentially continuous profile, as depicted diagrammatically at the left side of FIG. 2, from the lower rim 16 to a location L spaced upwardly from the rim 16 about one-half the distance D between the rim 16 and the apical region 18. The upper spherical surface portion 24 extends upwardly from the intermediate location L to the apical region 18. The lower spherical surface portion 22 has a radius R measured from an origin 28 located on the central axis C of the shell component 12 and spaced downwardly a short distance Y from the plane P of lower rim 16 so that the origin 28 is located outside the envelope of the shell component 12. Upper spherical surface portion 24 has a radius S measured from an origin coincident with origin 28. Radius R of the lower spherical surface portion 22 is slightly greater than radius S of the upper spherical surface portion 24, and a smooth transition is provided between the lower and upper spherical surface portions 22 and 24 in the vicinity of intermediate location L, as seen at 29. Lower spherical surface portion 22 preferably is knurled, as indicated at 30, or is provided with an alternate affixation-assisting surface treatment, for purposes which will be described more fully hereinafter.

Referring now to FIG. 3, the acetabulum 40 of a hip bone 42 has been provided with a surface contour for the reception of shell component 12. Thus, acetabulum 40 is prepared by forming an inner spherical surface 44, as by reaming with a spherical reamer (not shown) to the full desired depth D' of the acetabulum. Spherical surface 44 is provided with a radius S' which is essentially equal to radius S of the upper spherical surface portion 24 of the outer surface 20 of the shell component 12. Thus, the radius S' at the mouth 50 of the prepared acetabulum 40 is slightly smaller than the radius R of the lower spherical surface 22 of shell component 12. Depth D' is essentially equal to distance D of the shell component 12.

It is noted that in the surgical environment the preparation of the acetabulum 40 is carried out with hand-held instruments, so that ordinarily it is difficult to maintain the desired precision in the relationship between the surfaces of the prepared acetabulum and the shell component to be implanted in the prepared acetabulum. In particular, it is necessary to assure that the central axis C of the shell component 12 will be oriented properly with respect to the hip bone 42 when the shell component 12 is seated within the acetabulum 40, and that orientation usually must be taken into account during preparation of the acetabulum. However, since the inner surface of the acetabulum 40 is the spherical surface 44, the orientation of the spherical reamer which prepares spherical surface 44 is independent of the orientation of the seated cup component 12 and the preparation of the acetabulum 40 is simplified. That is, the hand-held spherical reamer may be held at any angular orientation during preparation of the spherical surface 44 without affecting the ultimate orientation of the implanted cup component 12, so that orientation of the reamer is not critical, thereby facilitating preparation of the acetabulum 40.

Figure 4:
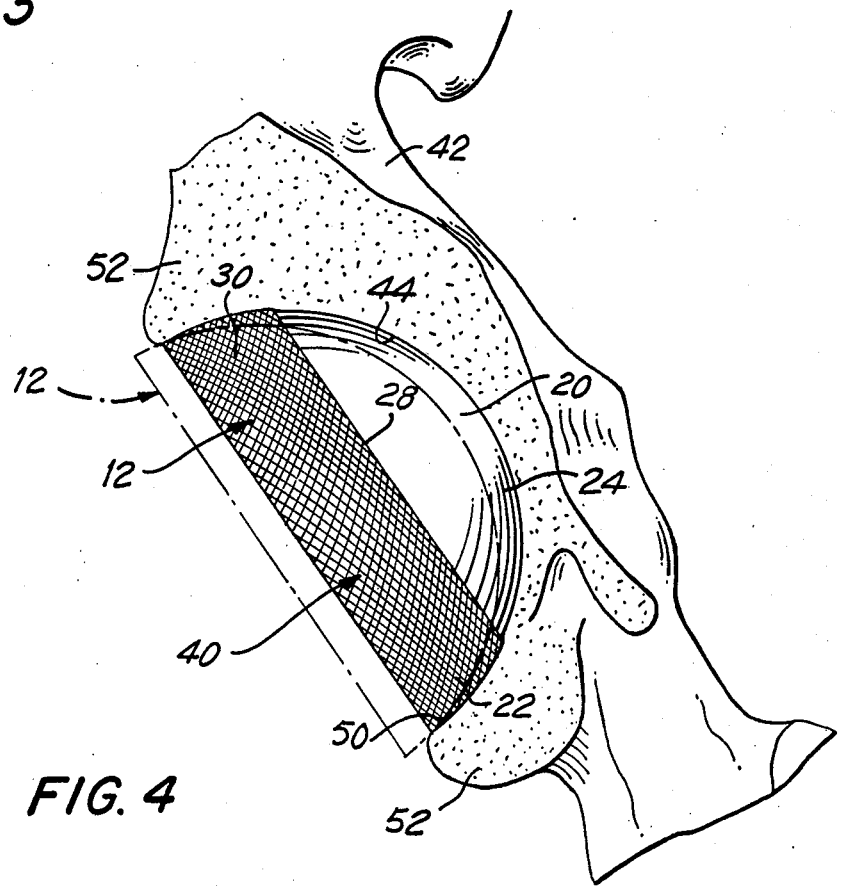
FIG. 4 is an illustration similar to FIG. 3, but showing the implant and securement of the shell component.

Turning now to FIG. 4, shell component 12 initially is placed in the prepared acetabulum 40 in the position shown in phantom, with the upper spherical surface portion 24 of outer surface 20 within the acetabulum 40 and the lower spherical surface portion 22 against the mouth 50 of the acetabulum 40. Subsequently, the shell component 12 is impacted into the acetabulum 40, utilizing available surgical instruments provided for that purpose, as illustrated in full lines, to achieve a tight, stable interference fit by virtue of the relative dimensions of the lower spherical surface portion 22 of the outer surface 20 of the shell component 12 and the spherical surface 44 of the acetabulum 40 at the acetabular rim 52 adjacent the mouth 50. At the same time, the upper spherical surface portion 24 and spherical surface 44 are placed in a contiguous nested relationship to attain the desired apposition between the shell component 12 and the acetabulum 40. The implant procedure is facilitated and the desired apposition is attained more readily by the dual-radius configuration of the outer surface 20, which configuration provides a relatively smooth transition between the lower spherical surface portion 22 and the upper spherical surface portion 24 in the vicinity of intermediate location L.

It is noted that the lower spherical surface portion 22 of the cup component 12 is located in the acetabular rim 52 upon completion of the implant. Thus, the interference fit between the cup component 12 and the acetabulum 40 is placed within a region of optimal bone structure for the accommodation of the interference fit. At the same time, the desired apposition between the upper spherical surface portion 24 and the prepared acetabulum 40 is attained by virtue of the congruity achieved by the fact that radius S and radius S' are equal. The shell component 12 is secured within the acetabulum 40 against rotation about the axial direction, against axial displacement and against rocking movements. The configuration of the outer surface contour 26 of shell component 12 assures such firm securement while requiring only minimal bone removal in the preparation of the acetabulum 40. The knurled or other affixation-assisting surface treatment at 30 assists in fixing the shell component 12 in place. A further affixation-assisting surface treatment (not shown) may be provided along the upper spherical surface portion 24 to assist in attaining affixation along the nested surfaces of the cup component 12 and the acetabulum 40. In addition, location of the lower spherical surface portion 22 of the shell component 12 within the acetabular rim 52 provides a transfer of the load placed on the shell component 12 resembling the natural load transfer.

Shell component 12 is manufactured in a range of sizes. Typically, the diameter of the spherical surface 44 will range from about 40 mm to 72 mm. It has been found that a difference of only about 0.5 mm between the radius R of the lower spherical surface portion 22 and the radius S of the upper spherical surface portion 24, when employed in combination with an acetabulum 40 within the range of the aforesaid dimensions, is sufficient to accomplish an interference fit having the qualities outlined above without introducing deleterious or intolerable stress in the surrounding bone structure. It is noted that the term "approximately one-half the distance D" as employed to define the axial extent of the lower spherical surface portion 22 relative to the axial extent of the upper spherical surface portion 24 denotes the ability to depart slightly from the nominal one-half the distance D while still attaining adequate performance.

It is to be understood that the above detailed description of a preferred embodiment of the invention is provided by way example only. Various details of design and construction may be modified without departing from the true spirit and scope of the invention as set forth in the appended claims.

The embodiments of the invention on which an exclusive property or privilege is claimed are defined as follows.

1. A shell component for use in an acetabular cup assembly of a prosthetic joint, the shell component having a dual-radius outer surface contour configured for implant into an acetabulum and securement therein by an interference fit, the shell component comprising:
   a lower rim;
   an apical region spaced upwardly in an axial direction a given distance from the lower rim;

an intermediate location spaced approximately one-half the distance between the lower rim and the apical region; and an outer surface having a first generally spherical surface portion extending upwardly from the lower rim to the intermediate location, and a second generally spherical surface portion extending upwardly from the intermediate location to the apical region, the first generally spherical surface portion having a radius slightly greater than the radius of the second generally spherical surface portion.

2. The invention of claim 1 wherein the difference between the radius of the first generally spherical surface portion and the radius of the second generally spherical surface portion is approximately 0.5 mm.

3. The invention of claim 2 wherein the first generally spherical surface portion includes an affixation-assisting surface treatment.

4. The invention of claim 1 wherein the shell component has a central axis and the origin of the radius of the first generally spherical surface portion is located along the central axis, spaced downwardly in an axial direction from the lower rim.

5. The invention of claim 4 wherein the origin of the radius of the second generally spherical surface portion is coincident with the origin of the radius of the first generally spherical surface portion.

6. The invention of claim 5 wherein the difference between the radius of the first generally spherical surface portion and the radius of the second generally spherical surface portion is approximately 0.5 mm.

7. The invention of claim 1 wherein the first generally spherical surface portion includes an affixation-assisting surface treatment.

8. An acetabular cup having a unitary dual-radius outer surface contour configuration for implant into an acetabulum and securement therein by an interference fit, the acetabular cup having a lower rim, an apical region spaced upwardly in an axial direction a given distance from the lower rim, an intermediate location spaced approximately one-half the distance between the lower rim and the apical region, and an outer surface extending between the lower rim and the apical region, the outer surface contour configuration comprising:

a first generally spherical portion extending upwardly between the lower rim and the intermediate location; and a second generally spherical portion extending upwardly between the intermediate location and the apical region;

the first generally spherical portion having a radius slightly greater than the radius of the second generally spherical portion.

9. The invention of claim 5 wherein the difference between the radius of the first generally spherical portion and the radius of the second generally spherical portion is approximately 0.5 mm.

10. The invention of claim 9 wherein the first generally spherical portion includes an affixation-assisting surface treatment.

11. The invention of claim 8 wherein the acetabular cup has a central axis and the origin of the radius of the first generally spherical portion is located along the central axis, spaced downwardly in an axial direction from the lower rim.

12. The invention of claim 11 wherein the origin of the radius of the second generally spherical portion is coincident with the origin of the radius of the first generally spherical portion.

13. The invention of claim 12 wherein the difference between the radius of the first generally spherical portion and the radius of the second generally spherical portion is approximately 0.5 mm.

14. The invention of claim 8 wherein the first generally spherical portion includes an affixation-assisting surface treatment.

* * * * *

REEXAMINATION CERTIFICATE (3886th)

United States Patent [19]
Figgie, III et al.

[11] B1 4,892,549
[45] Certificate Issued Oct. 5, 1999

[54] DUAL-RADIUS ACETUBULAR CUP COMPONENT

[75] Inventors: Harry E. Figgie, III, Pepper Pike, Ohio; Alfred J. Zarnowski, North Plainfield; Matthew V. Lyons, Hoboken, both of N.J.

[73] Assignee: Stryker Corporation, Kalamazoo, Mich.

Reexamination Request:
No. 90/004,779, Oct. 2, 1997

Reexamination Certificate for:
Patent No.: 4,892,549
Issued: Jan. 9, 1990
Appl. No.: 07/304,752
Filed: Jan. 31, 1989

[51] Int. Cl.⁶ ..................................... A61F 2/34
[52] U.S. Cl. ............................................ 623/22
[58] Field of Search ................. 623/16, 18, 22, 623/23

[56] References Cited

U.S. PATENT DOCUMENTS

| | | |
|---|---|---|
| 3,806,960 | 4/1974 | Weber . |
| 3,808,606 | 5/1974 | Tronzo . |
| 3,820,167 | 6/1974 | Sivash . |
| 3,829,904 | 8/1974 | Ling et al. . |
| 3,840,904 | 10/1974 | Tronzo . |
| 3,848,272 | 11/1974 | Noiles . |
| 3,859,669 | 1/1975 | Shersher . |
| 3,875,593 | 4/1975 | Shersher . |
| 3,891,997 | 7/1975 | Herbert . |
| 4,004,581 | 1/1977 | Heimke et al. . |
| 4,068,324 | 1/1978 | Townley et al. . |
| 4,274,164 | 6/1981 | Rehder et al. . |
| 4,279,041 | 7/1981 | Buchholz . |
| 4,302,855 | 12/1981 | Swanson . |
| 4,318,191 | 3/1982 | Tepic . |
| 4,408,360 | 10/1983 | Keller . |
| 4,437,193 | 3/1984 | Oh . |
| 4,596,580 | 6/1986 | Weill . |
| 4,623,352 | 11/1986 | Oh . |
| 4,662,891 | 5/1987 | Noiles . |
| 4,666,448 | 5/1987 | Ganz . |
| 4,685,923 | 8/1987 | Mathys . |

(List continued on next page.)

FOREIGN PATENT DOCUMENTS

| | | |
|---|---|---|
| 0 065 482 | 11/1982 | European Pat. Off. . |
| 0 291 562 | 11/1988 | European Pat. Off. . |
| 2 590 478 | 5/1987 | France . |
| 26 45 101 | 6/1978 | Germany . |
| 33 41 723 | 3/1985 | Germany . |
| 1 527 498 | 10/1978 | United Kingdom . |

OTHER PUBLICATIONS

"Development And First Experience With An Uncemented Press–Fit Cup" E. Morscher, M.D. and Z. Masar, M.D., Clinical Orthopaedics and Related Research No. 232, Jul. 1988.

Jul. 5, 1990 European Search Report (Preliminary Search Report) relating to EP 0 381 351.

Sep. 10, 1997 Letter from Smith & Nephew Richards including copy of DE 3,341,723 to Ganz, an English translation of DE 3,341,723 and a partial copy of a Smith & Nephew Richards application for patent.

*Primary Examiner*—David J Isabella

[57] ABSTRACT

An acetabular cup has a shell component with an outer surface including a first spherical surface portion and a second spherical surface portion, and an acetebulum is prepared with an inner surface having a spherical configuration complementary to the second spherical surface portion of the shell component, the radius of the first spherical surface portion being slightly greater than the radius of the second spherical surface portion such that upon nesting of the second spherical surface portion of the shell component in contiguous relationship with the inner surface of the acetabulum the first spherical surface portion engages the inner surface of the acetabulum in an interference fit to secure the shell component within the prepared acetabulum.

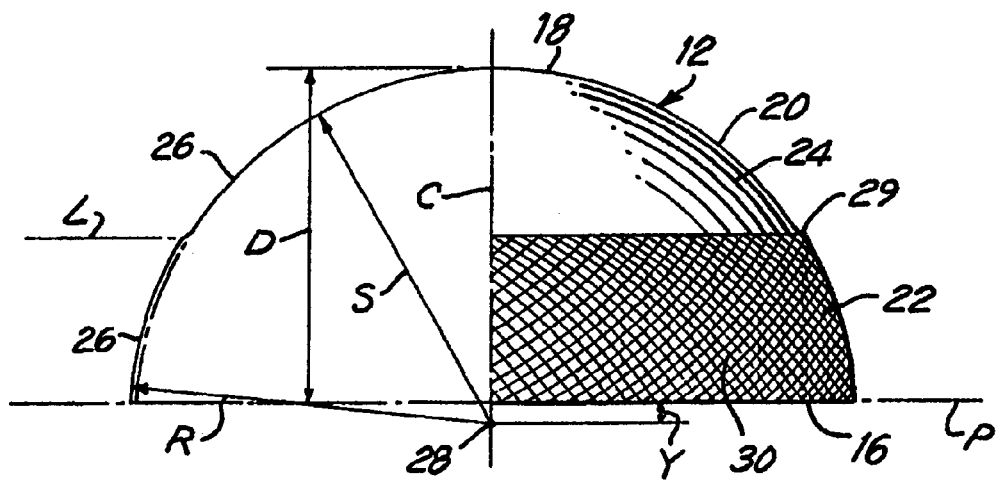

U.S. PATENT DOCUMENTS

| | | |
|---|---|---|
| 4,687,487 | 8/1987 | Hintermann . |
| 4,695,282 | 9/1987 | Forte et al. . |
| 4,704,127 | 11/1987 | Averill et al. . |
| 4,715,859 | 12/1987 | Schelhas et al. . |
| 4,715,860 | 12/1987 | Amstutz . |
| 4,769,041 | 9/1988 | Morscher . |
| 4,795,469 | 1/1989 | Oh . |
| 4,795,470 | 1/1989 | Goymann et al. . |
| 4,813,959 | 3/1989 | Cremascoli . |
| 4,834,759 | 5/1989 | Spotorno et al. . |
| 4,871,368 | 10/1989 | Wagner . |
| 4,878,916 | 11/1989 | Rhenter et al. . |
| 4,883,490 | 11/1989 | Oh . |
| 4,883,491 | 11/1989 | Mallory et al. . |
| 4,963,154 | 10/1990 | Anapliotis et al. . |

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *